United States Patent [19]

Kramer

[11] Patent Number: 5,442,111

[45] Date of Patent: Aug. 15, 1995

[54] 3,5-DI-TETRIARY-4-BUTYL-4-HYDROXY-PHENYLOXY- OR TIOALKYLENE N-HYDROXYAMIDES, N-HYDROXYTHIOAMIDES, N-HYDROXYUREAS, AND N-HYDROXYTHIOUREAS AS 5-LIPOXYGENASE INHIBITORS

[75] Inventor: James B. Kramer, Sylvania, Ohio

[73] Assignee: Warner-Lambert Company, Morris Plains, N.J.

[21] Appl. No.: 705,480

[22] Filed: May 24, 1991

[51] Int. Cl.⁶ .................................... C07C 335/12
[52] U.S. Cl. .................................... 562/623; 564/28
[58] Field of Search .................. 562/623; 560/313; 514/587; 564/28

[56] References Cited

U.S. PATENT DOCUMENTS

| | | | |
|---|---|---|---|
| 4,755,524 | 7/1988 | Mueller et al. | 514/381 |
| 4,857,558 | 8/1989 | Mueller | 514/712 |
| 4,873,259 | 10/1989 | Summers, Jr. et al. | 514/470 |
| 4,981,865 | 1/1991 | Belliotti et al. | 514/482 |
| 5,017,604 | 5/1991 | Belliotti et al. | 514/482 |
| 5,036,157 | 7/1991 | Kneen et al. | 562/623 |
| 5,075,330 | 12/1991 | Belliotti et al. | 549/359 |

FOREIGN PATENT DOCUMENTS

| | | |
|---|---|---|
| 279263 | 8/1988 | European Pat. Off. . |
| 0279269 | 8/1988 | European Pat. Off. . |
| 405788 | 1/1991 | European Pat. Off. . |
| 0405788 | 1/1991 | European Pat. Off. . |

*Primary Examiner*—José G. Dees
*Assistant Examiner*—B. Frazier
*Attorney, Agent, or Firm*—Ronald A. Daignault; Charles W. Ashbrook

[57] ABSTRACT

3,5-Di-tertiary-butyl-4-hydroxyphenyloxy- or thioalkylene N-hydroxyamides, N-hydroxythioamides, N-hydroxyureas, and N-hydroxythioureas, and pharmaceutically acceptable base salts thereof, pharmaceutical compositions thereof, and methods of manufacture thereof are described. The compounds are said to be selective, potent 5-lipoxygenase inhibitors and useful in treating, for example, inflammatory and allergic conditions.

2 Claims, No Drawings

3,5-DI-TETRIARY-4-BUTYL-4-HYDROXY-PHENYLOXY- OR TIOALKYLENE N-HYDROXYAMIDES, N-HYDROXYTHIOAMIDES, N-HYDROXYUREAS, AND N-HYDROXYTHIOUREAS AS 5-LIPOXYGENASE INHIBITORS

BACKGROUND OF THE INVENTION

The present invention is directed to novel N-hydroxyamides, N-hydroxythioamides, N-hydroxyureas, and N-hydroxythioureas substituted by a di-tertiary-butyl(hydroxy)phenyloxy- or thioalkylene residue which are selective, potent inhibitors of 5-lipoxygenase enzyme, whereby they are useful as antiinflammatory, antiarthritic, and antiallergy agents.

European Patent Publication No. 405 788 describes di-tertiary-butyl(hydroxy)phenylthio substituted hydroxamic acid derivatives for treating arteriosclerosis by inhibiting LDL (Low Density Lipoprotein). Although the publication notes utilities for inflammation, allergies, and the like, there is no indication of the compounds having 5-lipoxygenase inhibiting activity.

Indole, benzofuran, and benzothiophene N-hydroxyamides, thioamide, urea, and thiourea derivatives are described in European Patent Publication No. 279 263 as lipoxygenase inhibiting compounds. On the other hand, 3,5-di-tertiarybutyl(hydroxy)phenyl thioethers as specific 5-lipoxygenase inhibitors are described in U.S. Pat. Nos. 4,755,524 and 4,857,558.

Thus, the combination of 3,5-di-tertiary-butyl(hydroxy)phenyl group with N-hydroxyamides, thioamides, ureas, or thioureas as selective 5-lipoxygenase inhibitors has not been taught.

SUMMARY OF THE INVENTION

Accordingly, the present invention is a compound of the formula I

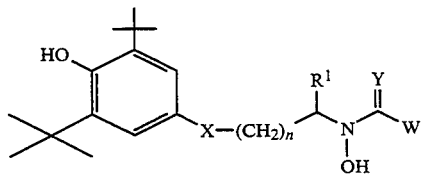

wherein
X is O, S, SO, or $SO_2$;
n is an integer of 1 to 4;
Y is S or O;
$R^1$ is hydrogen or lower alkyl, and
W is lower alkyl, phenyl, or phenyl substituted by one to three substituents selected from the group consisting of lower alkyl, lower alkoxy, halogen, and hydroxy, $NR^2R^3$ in which $R^2$ and $R^3$ are each independently hydrogen or lower alkyl, or $OR^4$ in which $R^4$ is lower alkyl when Y is O, or a pharmaceutically acceptable base salt thereof; with the proviso that when X is S and Y is O, W is $NR^2R^3$ or $OR^4$.

The present invention is also a pharmaceutical composition for the treatment of conditions advantageously affected by the inhibition of 5-lipoxygenase which comprises an amount effective for the treatment of the condition of a compound of the formula I and the pharmaceutically acceptable base salt thereof together with a pharmaceutically acceptable carrier. The condition is meant to include, for example, arthritis or other inflammatory diseases, allergic diseases, and psoriasis, but preferably inflammatory and allergic diseases.

The present invention is also a method for treatment of the condition as noted above in a mammal, including humans, suffering therefrom with a compound of the formula I or the pharmaceutically acceptable base salt thereof, in unit dosage form. The invention also provides for use of any such compound of formula I or salt thereof in the manufacture of a medical therapeutic agent.

Pharmaceutical composition or use of the compound or salt of formula I is meant to include treatment understood to be prophylactic pertinent to the foregoing named condition.

DESCRIPTION OF THE PREFERRED EMBODIMENTS

The term "lower" preceding "alkyl" or "alkoxy" as used to define compounds of formula I means a straight or branched hydrocarbon chain of one to six carbon atoms such as, for example, methyl, ethyl, n-propyl, isopropyl, n-butyl, sec-butyl, tertiary-butyl, n-pentyl, n-benzyl, and the like.

"Halogen" includes fluorine, chlorine, bromine, and iodine.

Appropriate compounds of formula (I) are useful in the free acid form or in the form of base salts where possible. The two forms are within the scope of the invention. In practice, use of the salt form amounts to use of the acid form. Pharmaceutically acceptable salts within the scope of the invention may be those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).) Salts of inorganic bases include sodium, potassium, calcium or the like.

A preferred embodiment is a compound of formula I wherein W is $NR^2R^3$, especially where X is S.

Particularly valuable are N-[2-[[3,5-bis(1,1-dimethylethyl)-4-hydroxyphenyl]thio]-1-methylethyl]-N-hydroxy-N'-methyl thiourea and N-[2-[[3,5-bis(1,1-dimethylethyl)-4-hydroxyphenyl]thio]-1-methylethyl]-N-hydroxy urea or a pharmaceutically acceptable base salt, e.g., choline or sodium.

In determining when a lipoxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula (I) or pharmacologically acceptable salt thereof to achieve a therapeutic effect will, of course, vary both with the particular compound, the route of administration, the mammal under treatment, and the particular disorder or disease concerned. A suitable dose of a compound of formula (I) or pharmacologically acceptable salt thereof for a mammal suffering from, or likely to suffer from any condition as described hereinbefore is 0.1 μg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 μg of the compound per kilogram, typically about 0.1 μg/kg.

In the case of oral dosing for the treatment or prophylaxis of arthritis or inflammation in general, due to any course, a suitable dose of a compound of formula (I) or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula (I) or a pharmacologically acceptable base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier thereof and optionally other therapeutic ingredient(s). The carrier (s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme or in treating related diseases or conditions may be demonstrated by their effectiveness in various standard test procedures. A description of the procedure follows.

ARBL WHOLE CELL 5-LIPOXYGENASE ASSAY

Materials

The rat basophilic leukemia cell line (RBL-1) was obtained from the American Type Culture Collection (Rockville, Md.).

A radioimmunoassay (RIA) kit of LTB was obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; NaHPO, 1.15 g; KHPO, 0.2 g; and KCl, 0.2 g/l). Cells are finally suspended in PBS containing 1.0 mM calcium at a density of $2 \times 10$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at $-20°$. Aliquots (100 μl) are analyzed for LTB using the radioimmunoassay kit as provided by the supplier.

The following table contains biochemical data obtained from this whole cell assay as a percentage of inhibition.

TABLE

| Example | Y | W | ARBL @ $10^{-6a}$ |
|---------|---|------|-------------------|
| 1 | S | NHCH$_3$ | 100% |
| 2 | O | NH$_2$ | 100% |

$^a$% inhibition for LTB$_4$

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives' as defined herein are nonnarcotic analgesics/nonsteroidal antiinflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH₂COOH group (which optionally can be in the form of a pharmaceutically acceptable salt group, e.g. —CHCOO⁻Na), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

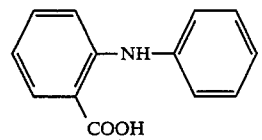

which can bear a variety of substituents and in which the free —COOH group can be in the form of a pharmaceutically acceptable salt group, e.g., —COO⁻Na.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

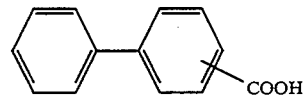

which can bear a variety of substituents and in which the free —COOH group can be in the form of a pharmaceutically acceptable salt group, e.g., —COO—Na⁺.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

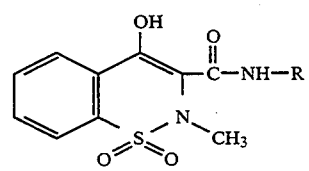

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, difisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an H or H-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a K/H ATPase inhibitor such as omeprazole, disclosed in U.S. Pat. No. 4,255,431, and the like. Each of the references referred to in this paragraph is hereby incorporated herein by reference.

Generally, the compounds of formula I are prepared by the following methods shown hereinafter in Schemes I to III. Although in each scheme the sequence may be illustrated with a compound wherein a variable may have been selected, it can be seen from the examples that other compounds of this invention can be prepared in the same manner using the appropriate starting materials.

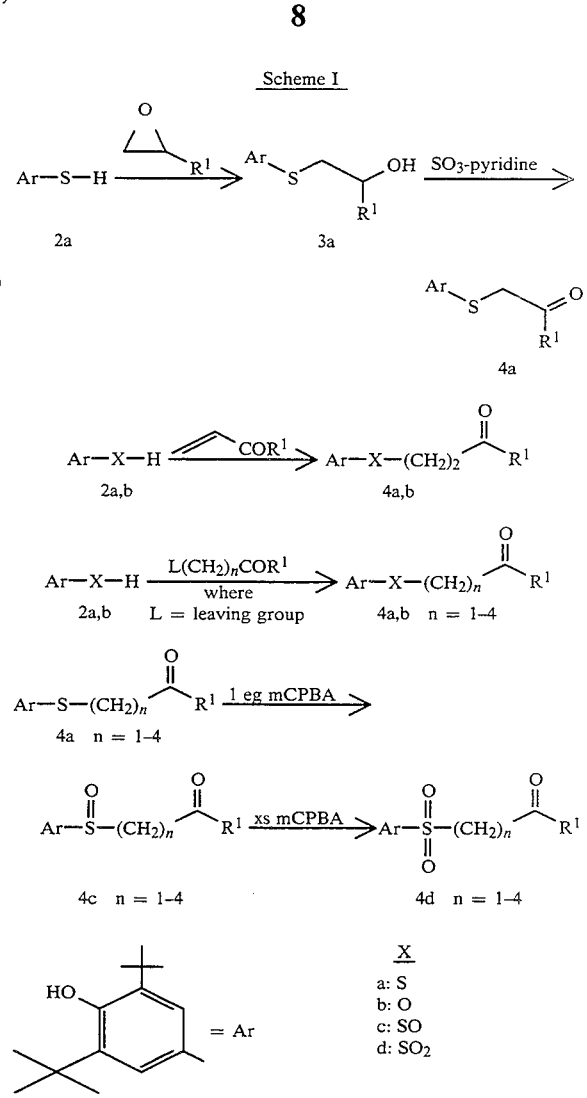

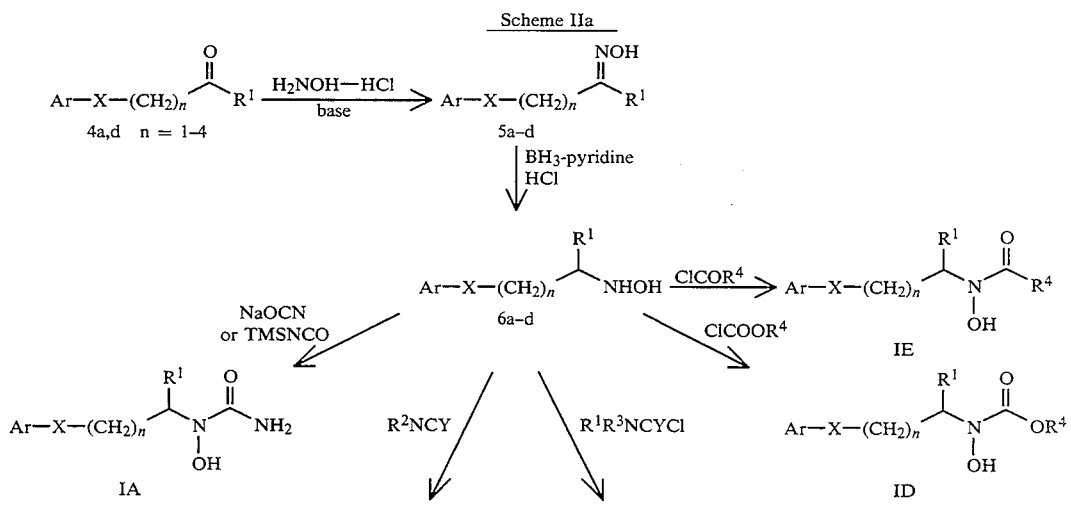

-continued
Scheme IIa

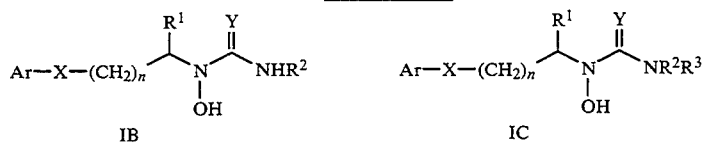

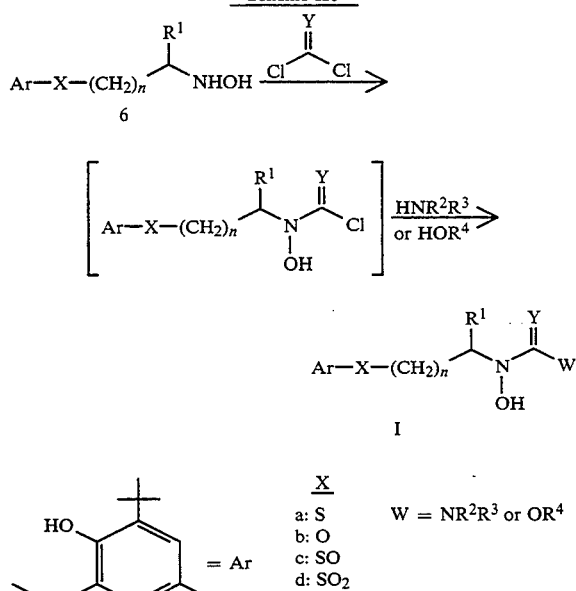

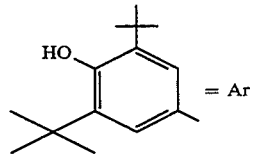

as the reduction of 2,6-di-t-butyl-1,4-benzoquinone with sodium borohydride (Matti Karhu, *J. Chem. Soc., Perkin Trans. I* (1981), 303) or with zinc dust/hydrochloric acid (U.S. Pat. No. 3,415,849); the Dakin Reaction on 3,5-di-t-butyl-4-hydroxybenzaldehyde (D. H. R. Barton, et al., *J. Chem. Soc.* (C), (1971), 1206 and references therein); and additional methods such as the Baeyer-Villager oxidation.

Compounds of type 4a, where n is 1 and X is S, are obtained from the treatment of the compound of type 2a, wherein X is S, with monosubstituted epoxides (U.S. Pat. No. 4,755,524) and a suitable base, preferably potassium carbonate in a suitable solvent such as methylene chloride, tetrahydrofuran, or preferably ethanol. The alcohol 3a is then oxidized to ketone 4a, utilizing mild oxidizing agents such as those of Swern or Moffatt, but preferably sulfur trioxide-pyridine complex (Hamada, *J. Org. Chem.*, 52(7), (1987), 1252).

Compounds of type 4a and b, where X is S or O and n is 2, can be prepared as described in U.S. Pat. Nos. 4,857,558 and 4,539,159 utilizing compounds containing an α,β-unsaturated carbonyl.

The compounds of type 2a and b, where X is S or O, can also be treated with a halogenated ketone (U.S. Pat. No. 4,857,558) such as chloroacetone or 5-chloro-2-pentanone, or a ketone substituted with another suitable leaving group like tosylate or mesylate, in the presence

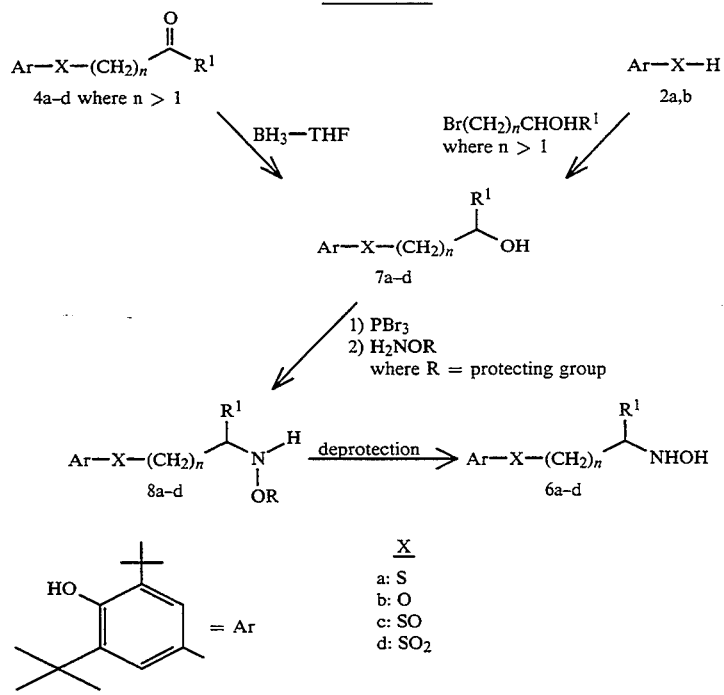

In Scheme I, the compounds of type 2a, where X is S, can be prepared by the method described in European Patent 0,293,900. The compound of type 2b, where X is O, can be prepared by various published methods such of a suitable base such as potassium carbonate, triethylamine, or preferably pyridine at an appropriate temperature of 0° C. to 100° C. to give compounds of type 4a or b. Suitable solvents for this reaction include methylene chloride, tetrahydrofuran, and dimethylformamide.

The ketones 4c and d can be prepared by the oxidation of the thioethers of type 4a. Utilizing one equivalent of peroxide or peracid, preferably meta-chloroperbenzoic acid in a solvent such as methylene chloride affords the sulfoxides of formula 4c. Use of two or more equivalents of the oxidizing agent affords the sulfones 4d.

As shown in Scheme IIa, the ketones of type 4a–d can be converted to the oximes 5a–d by treatment with hydroxylamine-hydrochloride and a suitable base such as triethylamine, sodium acetate, or preferably pyridine in a suitable solvent such as methylene chloride, tetrahydrofuran, or preferably an alcohol like ethanol. The reaction can be performed at −20° C. to 50° C. for 30 minutes to 7 days.

The oximes 5a–d are reduced to the hydroxylamines 6a–d with reducing agents such as sodium cyanoborohydride, borane:tetrahydrofuran, or preferably borane:pyridine complex in ether solvents such as diethyl ether or tetrahydrofuran or alcoholic solvents such as methanol, ethanol, or 2-propanol. The reduction is initiated by the addition of an acid such as hydrochloric acid.

Unsubstituted ureas of formula IA are prepared by the reaction of hydroxylamine 6a–d and sodium isocyanate initiated by a suitable acid, preferably hydrochloric acid, in a non-nucleophilic solvent such as tetrahydrofuran. This can also be accomplished with potassium isocyanate or trimethylsilyl isocyanate followed by ammonium chloride.

Monosubstituted thioureas and ureas of formula IB, where Y is S or O, are prepared by the reaction of hydroxylamine 6a–d and an alkylisothiocyanate or alkylisocyanate in a non-nucleophilic solvent, preferably tetrahydrofuran for 30 minutes to 7 days at 0° C. to 100° C.

Disubstituted compounds of formula IC, where Y is S or O, can be prepared from hydroxylamine 6a–d and a dialkylthiocarbamoyl chloride or dialkylcarbamyl chloride in the presence of a suitable base such as pyridine.

Compounds of formula ID can be prepared by treating hydroxylamine 6a–d with an alkyl chloroformate such as methyl chloroformate in a suitable solvent such as ethyl ether, tetrahydrofuran, or methylene chloride in the presence of a suitable base such as pyridine, triethylamine, or sodium acetate.

The compounds of formula IE can be prepared by treating hydroxylamine 6a–d with an acid chloride such as acetyl chloride in a solvent such as methylene chloride or tetrahydrofuran in the presence of a suitable base such as triethylamine or sodium acetate.

In addition the procedures illustrated in Scheme IIa, the compounds of formula IA through ID can be prepared by treating hydroxylamine 6a–d with phosgene or thiophosgene, or their equivalents followed by ammonia, primary or secondary amines, or alcohols as shown in Scheme IIb.

An alternative method to obtain the compounds of type 6a–d, where X is S, O, SO, or $SO_2$, and n>1, is illustrated in Scheme III. The alcohols of type 7a–d, where n > 1, can be prepared by the condensation of compound 2a or b with a bromo-alcohol in a suitable solvent such as methylene chloride in the presence of a suitable base such as triethylamine (U.S. Pat. No. 4,755,524), or by the reduction of the ketone 4a–d utilizing a reducing agent such as borne:tetrahydrofuran in tetrahydrofuran. The alcohols 7a–d are treated with phosphorous tribromide or bromotrimethylsilane in a solvent such as methylene chloride, followed by a hydroxylamine, preferably O-protected by tetrahydropyran or a trialkylsilane, affords compounds of type 8a–d. Suitable deprotection (U.S. Pat. No. 4,981,865) provides the hydroxylamines 6a–d.

The following examples are merely illustrative and show the preparation of representative compounds of formula I as well as starting materials used for their preparation.

PREPARATION OF STARTING MATERIALS

Example A 3,5-Bis(1,1-dimethylethyl)-4-hydroxyphenyl Thiocyanate

The titled compound was prepared according to the method of European Patent Publication 293 900.

EXAMPLE B 2,6-Bis(1,1-dimethylethyl)-4-mercaptophenol

The titled compound was prepared according to the method of European Patent Publication 293 900.

EXAMPLE C

1-[[3,5-Bis(1,1-dimethylethyl)-4-hydroxyphenyl]thio]-2-propanone

Chloroacetone (2.0 mL, 25.2 mM) is added to a 0° C. of 2,6-bis(1,1-dimethylethyl)-4-mercaptophenol (3.0 g, 12.6 mM) and pyridine (2.0 mL, 25.2 mM) in methylene chloride (100 mL). The reaction mixture is allowed to warm to room temperature then cooled again to 0° C., and an additional amount of chloroacetone (2.0 mL, 25.2 mM) and pyridine (2.0 mL, 25.2 mM) is added along with $K_2CO_3$ (100 mg). The reaction mixture is again allowed to warm to room temperature. The mixture is diluted with ethyl acetate and washed once with dilute aqueous hydrochloric acid, four times with water, and once with brine. The organic phase is dried over magnesium sulfate, filtered, and concentrated in vacuo. The residue is crystallized from ethyl acetate:hexane to give 2.8 g (75.5%) of white crystals, mp 105°–106° C.

EXAMPLE D 2,6-Bis(1,1-dimethylethyl)-4-[[2-hydroxyimino)propyl]thio]phenol

The reaction mixture of 1-[[3,5-bis(1,1-dimethylethyl)-4-hydroxyphenyl]thio]-2-propanone (1.0 g, 3.4 mM), pyridine (0.30 mL, 3.74 mM), and hydroxylamine hydrochloride (0.26 g, 3.74 mM) in ethanol (34 mL) is stirred at room temperature for 30 minutes. The mixture is then diluted with ethyl acetate and washed with water four times and once with brine. The organic phase is dried over magnesium sulfate, filtered, and concentrated in vacuo. The residue is chromatographed on silica gel, eluting with 15:85 ethyl acetate:hexane, giving 1.0 g (97%) of a white solid as a mixture of E and Z isomers.

EXAMPLE E

2,6-Bis(1,1-dimethylethyl)-4-[[2-hydroxyamino)-propyl]thio]phenol

A solution of 2,6-bis(1,1-dimethylethyl)-4-[[2-hydroxyimino)propyl]thio]phenol (0.50 g, 1.61 mM) and borane:pyridine complex (0.82 mL, 8.08 mM) in methanol (16 mL) is stirred for 10 minutes. Hydrochloric acid (6N, 1.35 mL, 8.08 mM) is added slowly, and stirring is continued for 2 hours. The reaction solution is diluted with ether and carefully washed with water four times, twice with a saturated solution of sodium bicarbonate, and once with brine. The organic phase is dried over magnesium sulfate, filtered, and concentrated in vacuo. The residue is chromatographed on silica gel, eluting with methanol:chloroform (1:99 then 2:98) to give 0.85 g (84%) of a white solid, mp 149°–153° C.

EXAMPLE 1

N-[2-[[3,5-Bis(1,1-dimethylethyl)-4-hydroxyphenyl]thio]-1-methylethyl]-N-hydroxy-N'-methyl Thiourea A solution of methyl isothiocyanate (61 mg, 0.83 mM) in tetrahydrofuran is added to a 0° C. solution of 2,6-bis(1,1-dimethylethyl)-4-[[2-hydroxyamino)propyl]thio]phenol (200 mg, 0.64 mM) in tetrahydrofuran. The reaction solution is stirred for 1 hour at 0° C. then for 1 hour at room temperature. The reaction solution is diluted with ether and washed three times with water and once with brine. The organic phase is dried over magnesium sulfate, filtered, and concentrated in vacuo. The residue is chromatographed on silica gel, eluting with 12:88 ethyl acetate:methylene chloride, then crystallized from methanol:water to give 196 mg (80%) of a white solid, mp 152°–153° C. (dec).

EXAMPLE 2

N-[2-[[3,5-Bis(1,1-dimethylethyl)-4-hydroxyphenyl]thio]-1-methylethyl]-N-hydroxy Urea Hydrochloric acid (6N, 0.53 mL, 3.20 mM) is added to a 0° C. suspension of 2,6-bis(1,1-dimethylethyl)-4-[[2-hydroxyamino)propyl]thio]phenol (200 mg, 0.64 mM) and sodium cyanate (208 mg, 3.20 mM) in tetrahydrofuran (6 mL). The reaction mixture is stirred at 0° C. for 30 minutes, then at room temperature for 1 hour. The solution is diluted with ether and washed once with dilute sodium bicarbonate, three times with water, and once with brine. The organic phase is dried over magnesium sulfate, filtered, and concentrated in vacuo. The residue is chromatographed on silica gel, eluting with 3:7 ethyl acetate: methylene chloride, then co-evaporated with ether:hexane to give 158 mg (70%) of a white solid, mp 65°–66° C.

I claim:

1. A compound of the formula

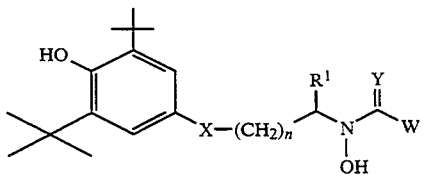

wherein

X is S;

n is an integer of 1 to 4;

Y is S;

$R^1$ is hydrogen or lower alkyl, and

W is $NR^2R^3$ in which $R^2$ and $R^3$ are each independently hydrogen or lower alkyl, or a pharmaceutically acceptable base salt thereof.

2. A compound according to claim 1 and being N-[2-[[3,5-bis-(1,1-dimethylethyl)-4-hydroxyphenyl]thio]-1-methylethyl]-N-hydroxy-N'-methyl thiourea.

* * * * *